(12) United States Patent
Rao et al.

(10) Patent No.: US 7,179,643 B2
(45) Date of Patent: Feb. 20, 2007

(54) DEVICE AND A PROCESS FOR EXPANSION OF HAEMOPOEITIC STEM CELLS FOR THERAPEUTIC USE

(75) Inventors: Sreemushnan Gopalkrishna Anando Rao, Mumbai (IN); Shabari Pradeep Tipnis, Mumbai (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 271 days.

(21) Appl. No.: 10/167,921

(22) Filed: Jun. 12, 2002

(65) Prior Publication Data

US 2003/0022363 A1    Jan. 30, 2003

Related U.S. Application Data

(60) Provisional application No. 60/298,175, filed on Jun. 14, 2001.

(51) Int. Cl.
*C12M 3/00* (2006.01)
(52) U.S. Cl. ............................. 435/299.2; 435/292.1; 435/303.1; 435/305.4; 435/809; 435/372
(58) Field of Classification Search ............. 435/372, 435/395–399, 299.1, 299.2, 303.1, 304.1–304.3, 435/305.1, 305.4
See application file for complete search history.

(56) References Cited

U.S. PATENT DOCUMENTS

| | | | | |
|---|---|---|---|---|
| 4,183,322 A | * | 1/1980 | Shultz et al. | 119/236 |
| 5,688,687 A | * | 11/1997 | Palsson et al. | 435/293.2 |
| 5,736,399 A | * | 4/1998 | Takezawa et al. | 435/399 |

FOREIGN PATENT DOCUMENTS

WO     WO 9915629 A1 *  4/1999

\* cited by examiner

*Primary Examiner*—William H. Beisner
(74) *Attorney, Agent, or Firm*—J. Harold Nissen; Lackenbach Siegel, LLP (57) ABSTRACT

A sterilizable bio-reactor comprising a three-dimensional reactor culture assembly substantially equivalent to a bone marrow micro environment, an inert bio-compatible scaffolding material located on a base of the reactor culture assembly to provide a micro environment identical to the micro environment in human bone marrow, for cultivating stem cells in the scaffolding, forming part of a sterilizable bio-reactor device, and a process for the expansion of haemopoietic stem cells derived from Human Umbilical Cord Blood for therapeutic use, comprising growing haemopoietic stem cells in the bio-degradable non-toxic bio-compatible scaffold while providing necessary nutrition and gasses cultivating the stem cells in the scaffolding material to provide for the cell growth in the bio reactor, and supplying mobilizing oxygen and carbon dioxide to maintain gas tension for optimal expansion of the stem cells, and circulating media containing micro and macro nutrients and growth factors to establish gradients within the enclosure.

16 Claims, 8 Drawing Sheets

DEVICE AND A PROCESS FOR EXPANSION OF HAEMOPOEITIC STEM CELLS FOR THERAPEUTIC USE

CROSS REFERENCE TO RELATED APPLICATION

This Application claims the benefit of the filing date of Provisional Patent Application Ser. No. 60/298,175, filed Jun. 14, 2001.

FIELD OF THE INVENTION

The present invention is related to a device which is a three dimensional bio-reactor and a process for expansion of haemopoietic stem cells derived from Human Umbilical Cord Blood for therapeutic use.

BACKGROUND OF INVENTION

The stem cell biologists describe the process of formation of blood as Haemopoiesis. This word is derived from the Greek root "haima" means blood and "poiesis" means to form. This process commences with the primitive haemopoietic stem cell. All blood cells originate from this cell. Stem cell transplantation has become an integral part of modern therapy. This regulated production of blood cells is one of the areas in biology most, amenable to scientific investigation. Blood cells, keratinocytes in skin & epithelium in gut have a short life span and are constantly renewed in specialized centres. The most discrete haemopoietic tissues are bone marrow, spleen, lymph nodes & thymus. Prenatally haemopoiesis also occurs in embryonic yolk sac from where it shifts to the liver and finally to the bone-marrow.

Haemopoiesis in mammals during embryonic & foetal development in humans is a migratory phenomenon. It begins in the foci of the yolk sac known as blood islands & migrates to the liver & spleen followed by bone marrow. The site of haemopoiesis varies with age. In the developing foetus, haemopoiesis commences in the yolk sac but after birth it is present solely in the bone marrow. In the infant, all the bone marrow space is filled with actively dividing haemopoietic cells and because of its red appearance (result of erythropoiesis) it is often called red marrow. This active haemopoiesis is necessary to meet the demands for blood cells by the growing child. It is noticed that with increase in age the amount of bone marrow space dedicated to haemopoiesis becomes restricted and active red marrow is replaced by fat cells and the marrow takes on a yellow appearance. The bone marrow is a richly cellular connective tissue within the bones of the body, specialized to produce blood cells & deliver them into circulation. It is the major haemopoietic tissue in human beings from the fifth week of foetal life through adulthood & accounts for about 5% of adult body weight. The cells of bone marrow consists of 1–2% of stem cells and the rest of differentiating and differentiated cells.

Haemopoietic stem cells are distinguished from other haemopoietic cells by their capacity to generate new stem cells, a process termed "self renewal" & their ability to proliferate & differentiate into different lineages thus clonally regenerating all the different types of blood cells. These processes of self renewal & differentiation are regulated by haemopoietic microenvironment. Haemopoietic stem cells comprise of a very small part of the haemopoietic system. These stem cells have an almost unlimited proliferative capacity which can be gauged by the fact that about $3.7 \times 10^6$ myeloid cells need to be produced every day of adult human life under normal conditions. During severe infections the demand for the differentiated end products of these cells may increase by 10 fold. Such a tremendous proliferative capacity needs very high regulation which is provided by the numerous cytokines acting in conjunction with each other & with other cell types regulating haemopoiesis through cell to cell contact. The bone marrow which is highly structured tissue is an ideal haven for this process to occur as it has the capacity to simultaneously provide different microenvironments to regulate the production of these cells as per the demands posed by the body.

As the bone marrow is the seat of haemopoiesis, transplantation of this marrow can be of therapeutic importance in various haematological diseases including malignancies. In recent years although significant advances have been made in bone marrow transplantion (BMT), the basic problem of finding a suitable matched donor still remains. This is because a group of antigens expressed by the leukocytes called human leukocyte antigens (HLA) need to match between the donor & the recipient. Also bone marrow harvesting is a painful & invasive procedure & it is difficult to get a suitable marrow donors as many donors are unwilling to donate their bone marrow. If bone marrow from a donor is used for a different person, the transplant is called an "allogeneic" BMT and when the bone marrow is used for an identical twin, the transplant is called "syngeneic" BMT. In an allogeneic BMT, it is essential that the new bone marrow infused into the patient matches with the genetic makeup of the patients own marrow as perfectly as possible. Special tests are conducted to determine whether or not the donor's bone marrow matches with the patient. The bone marrow transplant by conventional method requires the patient to be healthy enough to undergo the rigors of the transplant procedure. It requires an expert medical team who are well experienced in bone marrow transplant. It also requires providing patients and their families with emotional and psychological support before and after the transplant. The bone marrow is a debilitating experience. It can take as long as a year for the new bone marrow to function normally. Patients undergoing bone marrow transplant are closely monitored during this time to identify any infections or complications that can develop.

Looking to the problems associated with the bone marrow transplant stated above, alternative sources of stem cells are being investigated. The most important alternative source of haemopoietic stem cells is that derived from cord blood.

The cord blood as a source is advantageous to the traditional stem cell source i.e. the bone marrow, in the following ways:

1. The cord blood is much easier to obtain than bone marrow.
2. It can be collected immediately after birth of a child and does not interfere with normal delivery process.
3. The number of potential donors is high hence the question of getting a match for a patient does not arise.
4. The cord blood stem cells are naive and express HLA antigens poorly, especially the class II antigens, which are important in transplantation. As the antigens are poorly expressed, the two or three antigen mismatch does not result in graft versus host disease (GVHD) and the consequent rejection, thereby making the process of transplanting cord blood stem cells easier as compared to bone marrow transplantation.

A major limitation of using cord blood for transplantation is that the yield of stem cells may not be enough for transplantation in adults. This can however be overcome by the expansion technique described for a quantitative increase in the stem cell of small volume collections of cord blood. The collected sample sometimes does not contain enough cells for complete haemopoietic reconstitution of an adult. Thus, for a cord blood to become a viable transplantable source of stem cells these cells must be increased by expansion in vitro, without the loss in their stemness. The ability of haemopoietic stem cells to express an intrinsic expansion & proliferation potential in vitro depends on the cytokines present in a culture. Several stem cell populations depending on their maturity undergo extensive proliferation & differentiation in response to stimulation with different combinations of cytokines. Cytokine mediated expansion therefore has been proposed as a means of increasing the total number of cells as well as committed & primitive haemopoietic progenitors in cord blood (About 1994). However, it is noticed that cytokines mediated expansion compromise the long term repopulating capacity of stem cells.

Different techniques are being used for the expansion of stem cells from umbilical cord blood. Many Biotech companies already own dozens of patents on the culture techniques of stem cells. However, they suffer from some defects. The stem cells that are cultured, tend to lose their stemness/self-renewal property.

Looking to the increased therapeutic potential for stem cell isolation, the inventors of the present invention have developed a device/bioreactor and a process for expansion of stem cells, for therapeutic use, from cord blood without compromising their self-renewal property. The processes of self-renewal and differentiation are regulated by haemopoietic growth factors and haemopoietic microenvironment, which the device of the present invention has regulated, in a manner that the expansion system used retains and expands stem cells with long term repopulating potential.

A bio-reactor is a device for growing cells. The bioreactor of the present invention has a scaffolding material placed on the base of the culture vessel. It is the scaffolding material that provides the microenvironment substantially identical to that present in the human bone marrow. The scaffolding material is porous in nature with sufficient internal space for the stem cells to grow. The device/bio-reactor of the present invention is easy to use, reproducible and particularly suitable for large scale cord blood processing under Good Manufacturing Practice (GMP) conditions.

OBJECT OF INVENTION

It is an object of the present invention to develop a three dimensional device/bioreactor for the expansion of haemopoietic stem cells from cord blood without compromising their self-renewal property.

It is further object of the present invention to develop a device/bioreactor for expansion of haemopoietic stem cells which are genetically engineered.

It is further object of the present invention to develop a device/bioreactor that is easy to use, safe and economically viable.

It is still further object of the present invention to develop a disposable device/bioreactor having a single use.

It is still further object of the present invention to develop a process for expansion of haemopoietic stem cells without loosing their stemness.

SUMMARY OF INVENTION

The present invention provides a three dimensional device/bioreactor designed for expansion of haemopoietic stem cells and a process thereof, for therapeutic use, from cord blood without compromising their self-renewal property. The inventors of the present invention have been successful in developing a three dimensional device/bioreactor designed for expansion of haemopoiefic stem cells without compromising their self-renewal property. The bioreactor of the present invention is a unique one and no body to the best of the knowledge of the inventors have developed such a bioreactor.

It is a known fact that the haemopoietic stem cells with infinite self-renewal are required for long term reconstitution of the haemopoietic system. These cells, however, constitute a small proportion of cells from the various stem cells source like cord blood, foetal liver & bone marrow. Since these cells are required in large number for therapeutic purpose, they need to be increased in number i.e. expanded in vitro. Long term repopulating haemopoietic stem cells need a unique micro environment, which includes close cell to cell interaction. The device of the present invention specially provides for such interaction, by growing these cells in the bio-degradable non-toxic bio compatible three dimensional scaffold providing necessary nutrition and gasses needed in a optimum way.

The problem existing in stem cell expansion in vitro is that the cytokines, which can proliferate these cells also differentiate them to lose self-renewal property. The existing method for expansion of stem cells suffer from this defect and the present invention has solved the existing defect as the reactor which is developed is designed in such a way that the self-renewal property of haemopoietic stem cells remains intact.

According to one aspect of the present invention is to provide a process for expansion of haemopoietic stem cells derived Umbilical Cord Blood, using a three dimensional bioreactor comprising of the following:

Collection of Cord Blood:

Cord blood is collected from full term deliveries after obtaining informed consent from pre-screened mothers. The mothers are screened for HIV, HbsAg, CMV, HBV and HCV. Cord blood is collected using blood collection bags containing CPDA (anti-coagulant). These bags are then transported to the processing laboratory with minimum delay.

Enrichment of Mononuclear Cells:

Red blood cell depletion is carried out using 3% v/v Dextran (high molecular weight) in the ratio of 1:1 with respect to the volume of blood. Leucocyte rich plasma is collected carefully and centrifuged. Cells are washed and layered on Histopaque™ 1077. The tubes containing the sample are centrifuged at 400 g for half an hour. Mononuclear cells (MNCs) are separated from the interface using pipettes. These cells are washed and counted. The MNCs are then suspended in the expansion medium containing Iscovic'c Modified Delbecco's Medium (IMDM), 10% Foetal Bovine Serum (FBS) and antibiotics at a concentration of $1 \times 10^6$/ml.

Setting Up of Bioreactor:

The separate parts of the bioreactor, as shown in the diagrams, are collected and sterilized (dry heat sterilization for glass and gamma sterilization for polycarbonate). The sterile parts of the bioreactor are taken in the laminar flow hood and opened under sterile conditions for use. The parts are assembled using sterile tubings as described in the figure. The clamps are attached so as to adjust the flow rate of the medium used for enrichment of Mononuclear cells (MNC). The cells are inoculated in the reactor vessel using a sterile needle and syringe. The specific growth factors are also added using a sterile needle and syringe. The medium is filled in the upper reservoir. The reactor is finally assembled in the persplex box as an individualized assembly. The flow rate is controlled using clamps attached on the sterile tubings. The entire assembly is then placed in the carbon dioxide ($CO_2$) incubator at 5% $CO_2$ and 37° C. for culturing of cells. The medium can be recycled till the cells are harvested.

Harvest of the Cells from the Bioreactor:

After the specific days of the culture, the cells in the bioreactor are ready for harvest. The assembly is taken in the laminar flow hood from the incubator. The medium is collected in a flask. The bioreactor is disassembled and all the parts are separated. The reactor vessel is removed in sterile conditions. The cells are collected in the sterile tube. The vessel is washed using sterile buffers and all the washings are collected together in the same tube. The cells are pelleted down and washed. These cells are resuspended in the medium and thereafter are counted manually as well as on an automated counter. These cells are then used for detecting the presence of CD34 marker by carrying out flow cytometry and clonogenic assay for detection of presence of CFU-GM colonies. These test are required for detecting the presence of hematopoietic stem cells, which are characterized by the presence of CD34 marker and colony forming progenitor cells.

Flow Cytometry:

The cells are used for staining with fluorescent stains for flow cytometry. Specified number of cells are taken in falcon round bottom tubes. These cells are stained with Anti-CD34 antibody. After staining, these cells are run on the flow cytometer (FACS Calibur). The cells are gated on forward v/s side scatter and the presence of CD34+ cells was observed in terms of percentage. The absolute number of CD34+ cells are also calculated using the two platform study.

Clonogenic Assays:

The harvested cells are also used for checking the presence of colony forming units for ganulocytes and macrophages (CFU-GM). $1 \times 10^5$ cells/ml are used for this purpose. The growth factors are added to the basal layer of the 0.8% methyl cellulose. The cells are added to the upper layer of 0.8% of methyl cellulose. These plates are incubated at 5% $CO_2$ and 37° C. temperature for 14 days. The plates are scored for colonies after 14 days. The number of colonies gives an idea about the presence of progenitor cells among the harvested cells.

According to another aspect of the present invention is to provide a three dimensional device/bioreactor for expansion of haemopoietic stem cells without compromising their self renewal property. The working of the bioreactor of the present invention is given below:

The haemopoietic stem cells are cultivated in an inert, bio-compatible scaffold, which provides cell growth in three dimensions. The scaffold used, has a property of complexing in a specific way with some protein needed for stem cell renewal. The scaffold used provides large area in the form of the internal space where the cells grow.

The device provides a gas inlet for mobilising oxygen and carbon dioxide thereby maintaining gas tension required for optimal expansion of haemopoietic stem cells. It also provides means for circulation of media containing micro & macronutrients and growth factors in a way that gradients essential for haemotopoietic stem cell expansion are established within the reactor body.

The reactor vessel is fitted in a "PERSPEX" or thick sheet plastic (a registered trademark, Registration Number 555,324) case provided with a gas inlet and then kept in a carbon dioxide incubator configured to receive and condition the device/bio-reactor during different stage of the cell growth process, unlike other reactor vessels which are kept directly in carbon dioxide incubator without being fitted in a case. Since the present reactor vessel is fitted in a case, many such cases can be mounted in carbon dioxide incubator without disturbing other assemblies. "Perspex" defines material which is plastic available in thick sheets.

The present device has overcome the cumbersome procedure of harvesting of stem cells by using proteolytic enzymes. The proteolytic enzymes result in the modification of stem cell surface characteristic, which are very important for their ability to home and engraft in marrow spaces. The present device allows the possibility of direct transplantation of the stem cells along with the scaffolding material in the bone marrow cavity by a minimally invasive technique, thereby obviating the cumbersome procedure of harvesting the stem cells.

The present device ensures the cultivation of stem cells in a sterile environment needed for therapeutic use. The device is a single use, disposable individualized unit.

BRIEF DESCRIPTION OF DRAWINGS

The invention will now be described in detail as it may be carried out in the device/bio-reactor shown in the Figures are in conjunction with detail description of the presently preferred embodiments of the invention wherein:

FIG. 2 is the top view of the bioreactor. It gives the dimensions of the entire bioreactor along with the casing in accordance with a preferred embodiments of the present invention.

FIG. 3 is a elevational side view of the bioreactor. The figure shows all the joints and parts of the reactor along with the clamps to which the parts of the reactor are attached.

FIG. 4 is an exploded view of the structure of the reservoir for the media. It is a graduated vertical vessel with one inlet and three outlets. The reservoir is 100 cc. in volume, made up of glass or biocompatible polymer eg. polycarbonate. This volume can be increased in scale-up models.

FIG. 7 is an exploded view of the reactor vessel with one outlet. The vessel is provided with a facility to place the scaffolding matrix for growing cells at a height of 1 mm from the base of the vessel. The outlet is provided 1 mm above the scaffold, so that some volume of media is always present above the scaffold to prevent drying of cells. A filter is attached at this outlet to prevent the detached cells from being removed or washed off from the reactor vessel. The outflow of media is gravity dependent, so that the process of outflow does not disturb the cells growing in the scaffolding area.

DESCRIPTION OF THE PREFERRED EMBODIMENT

Figure 1:
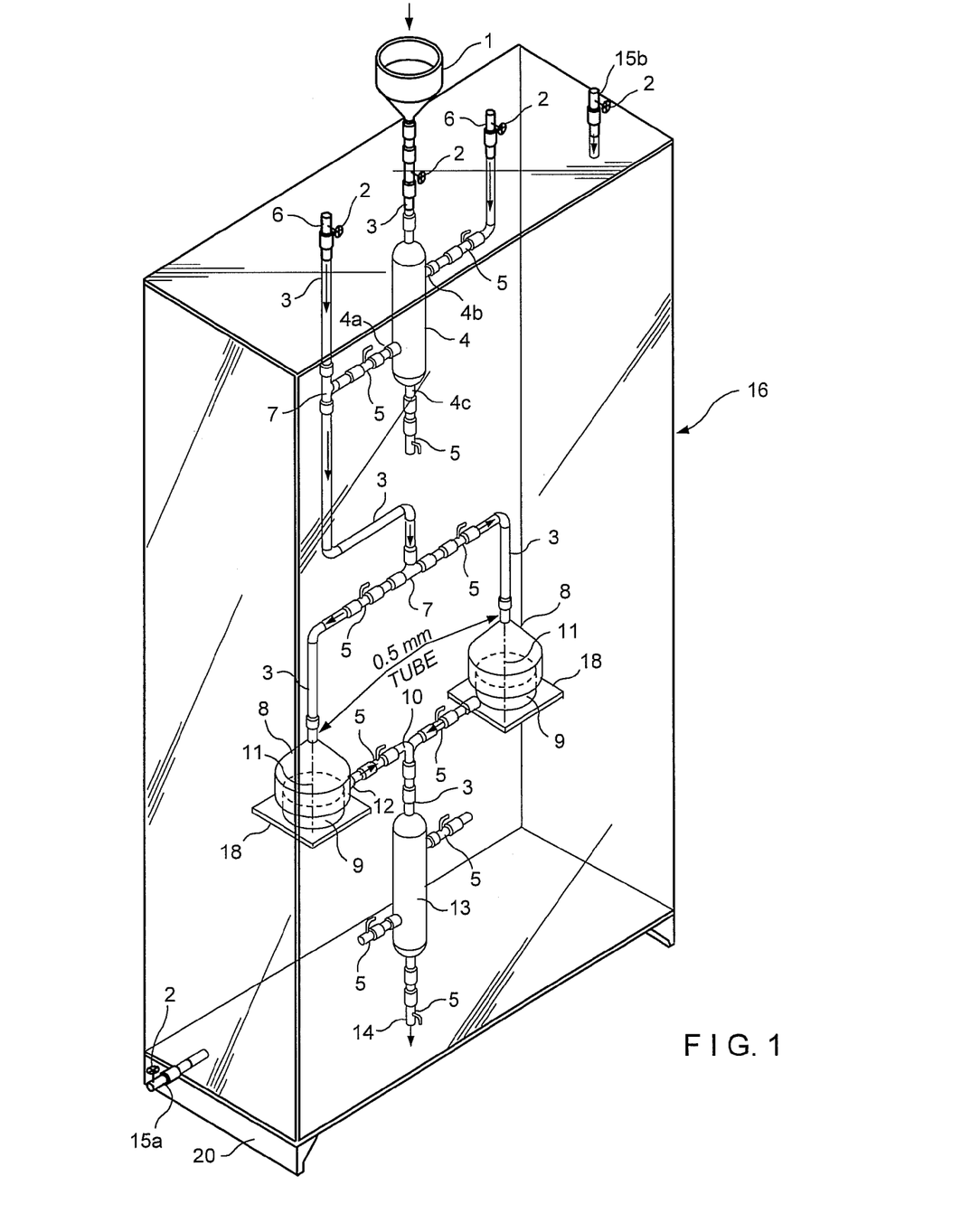
FIG. 1 is schematic diagram of a bioreactor in accordance with the invention, including a reservoir, reactor vessel placed on a support and a used media collector. The present invention is mainly useful for growing heamopoietic stem cells from cord blood in a three dimensional structure.
Figure 1A:
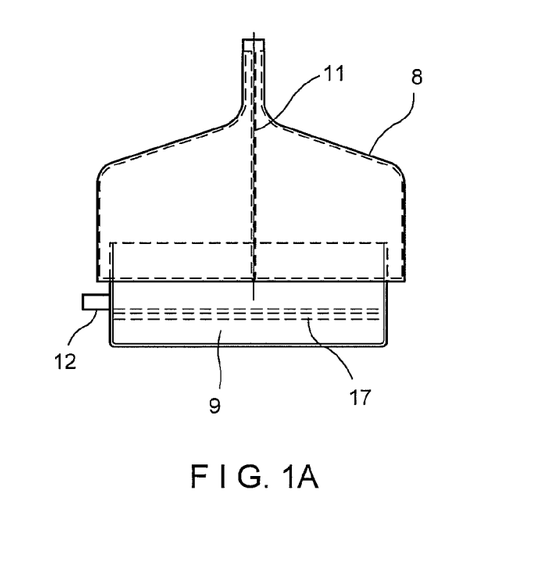
Figure 2:
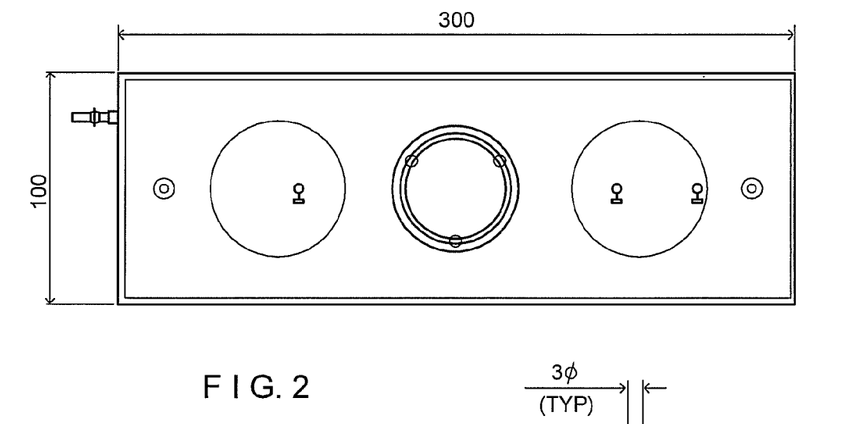
Figure 3:
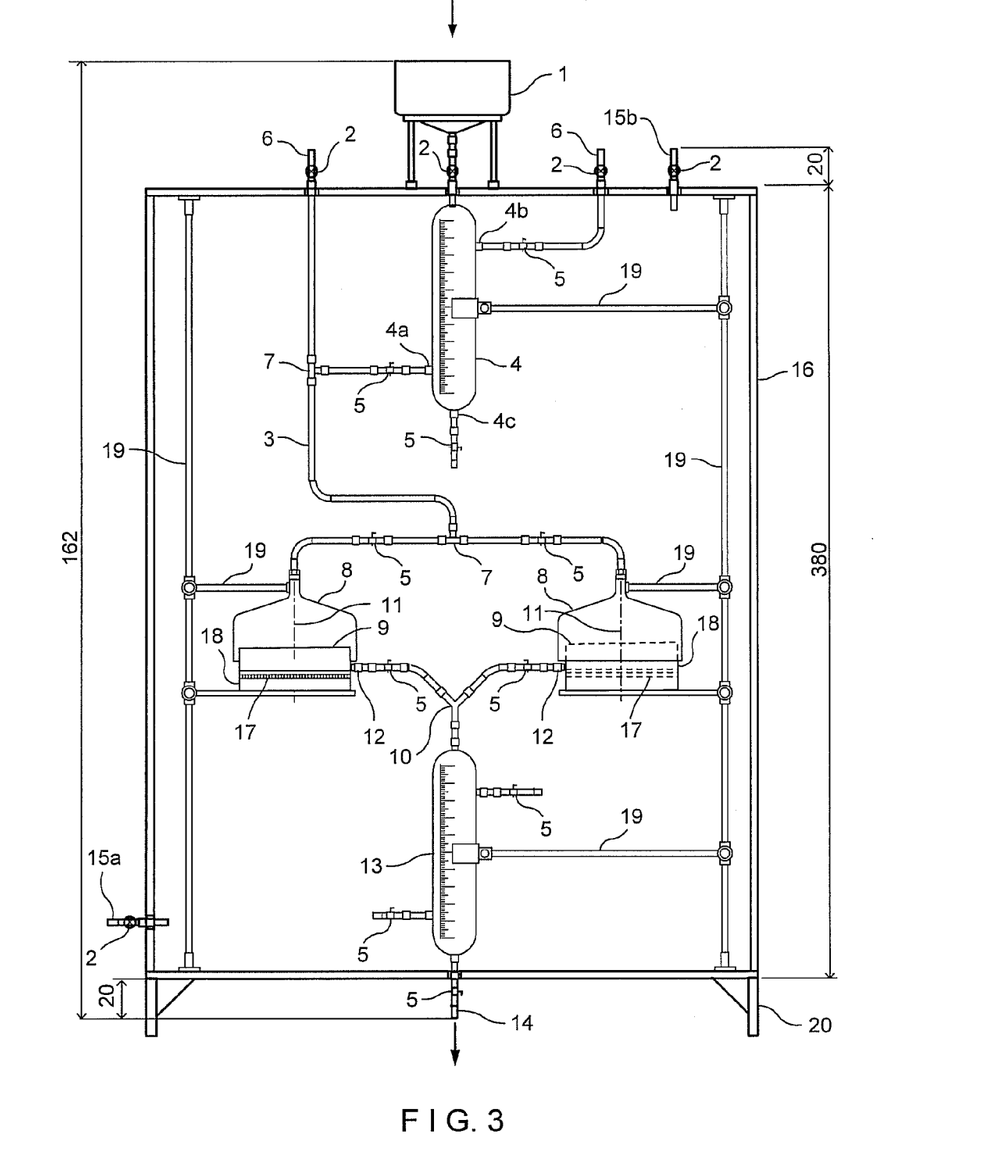
Figure 4:
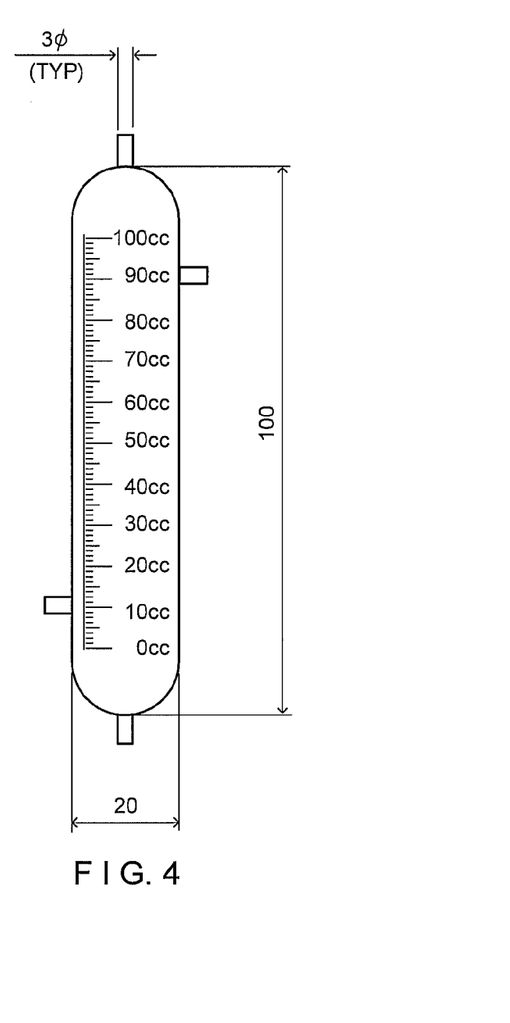
Figure 5:
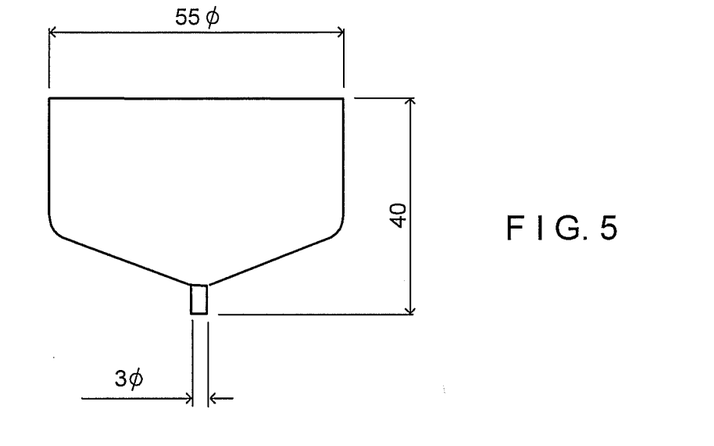
FIG. 5 is an exploded view of inlet for media. This is attached to the reservoir at the inlet point and is made up of glass or biocompatible polymer like polycarbonate.
Figure 6:
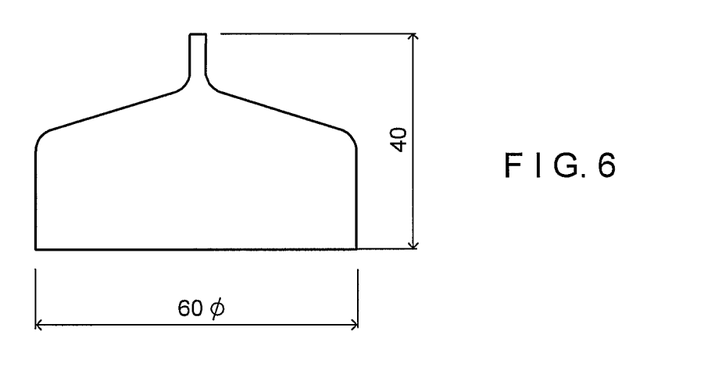
FIG. 6 is an exploded view of the reactor body cover to which a glass capillary is fused. This cover is mounted above the reactor vessel so as to allow free exchange of gases.
Figure 7:
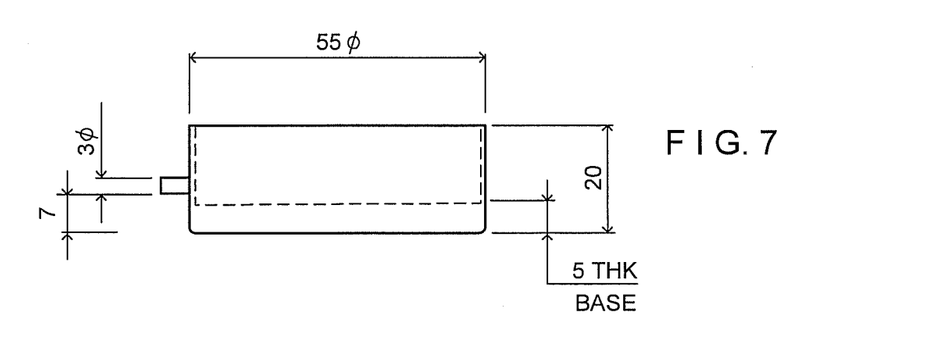
Figure 8A:
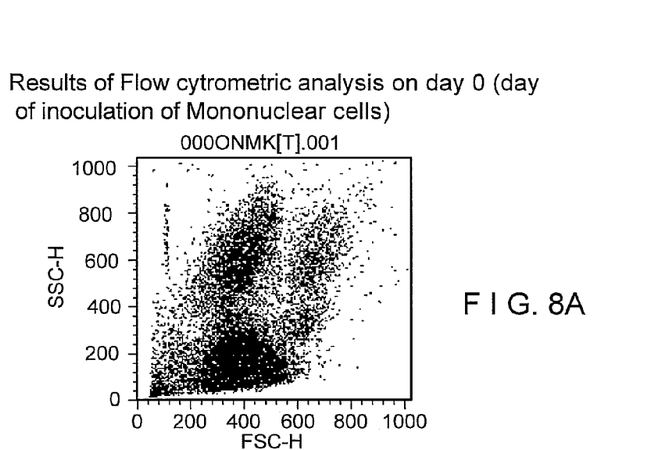
FIGS. 8A, 8B, 8C and 8D illustrate the results of the flow cytometric analysis on day zero and day of inoculation of mononuclear cells.
Figure 8B:
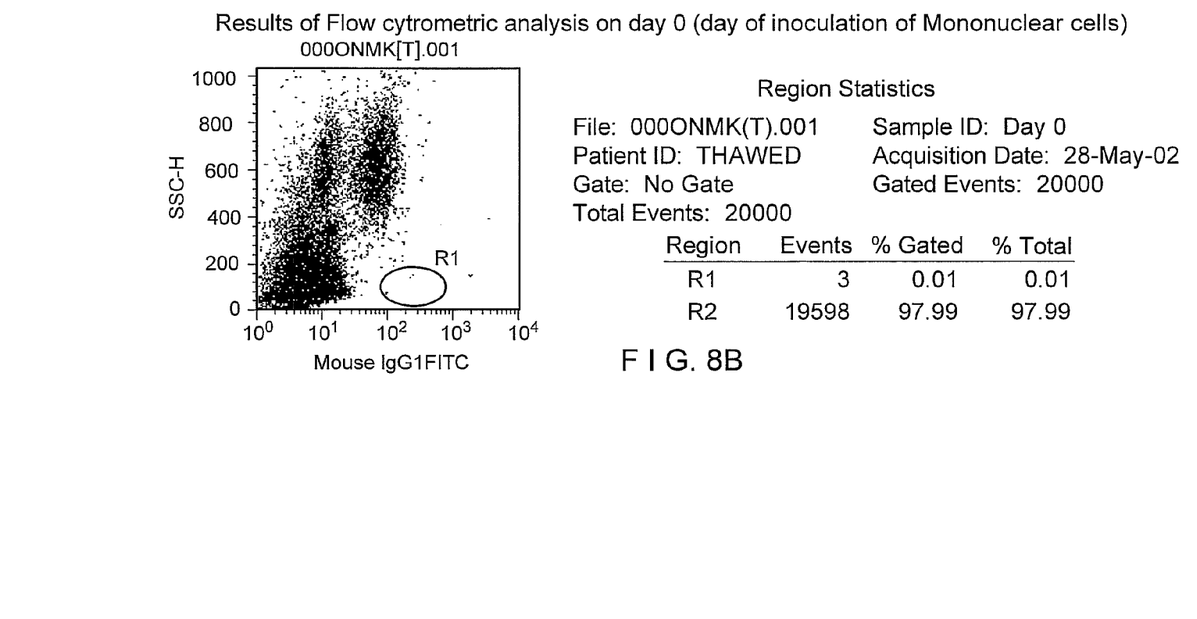
Figure 8C:
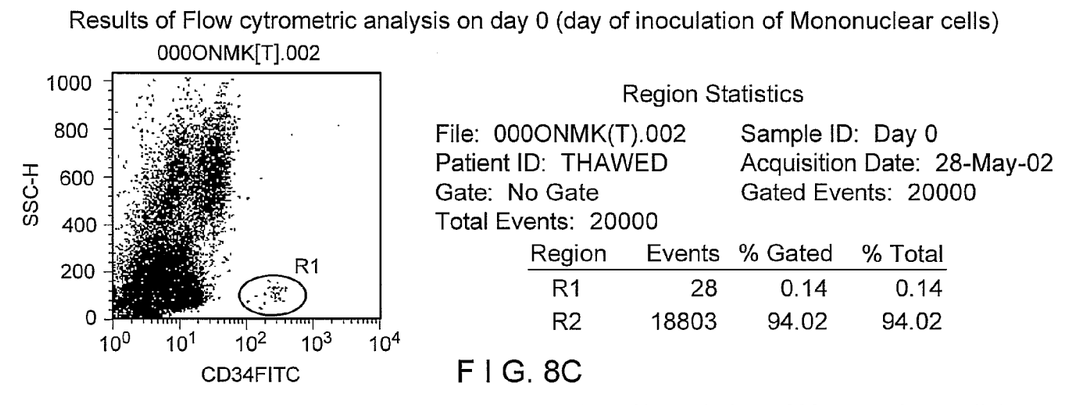
Figure 8D:
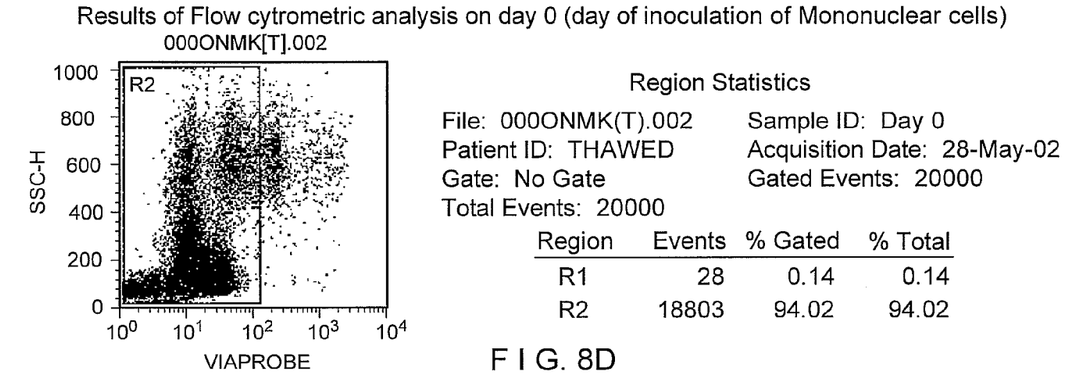
Figure 9A:
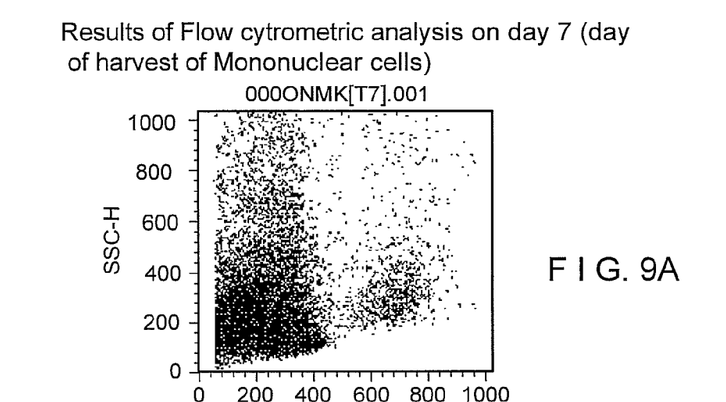
FIGS. 9A, 9B, 9C and 9D illustrate results of flow cytometric analysis on day 7 and day of harvest of mononuclear cells.
Figure 9B:
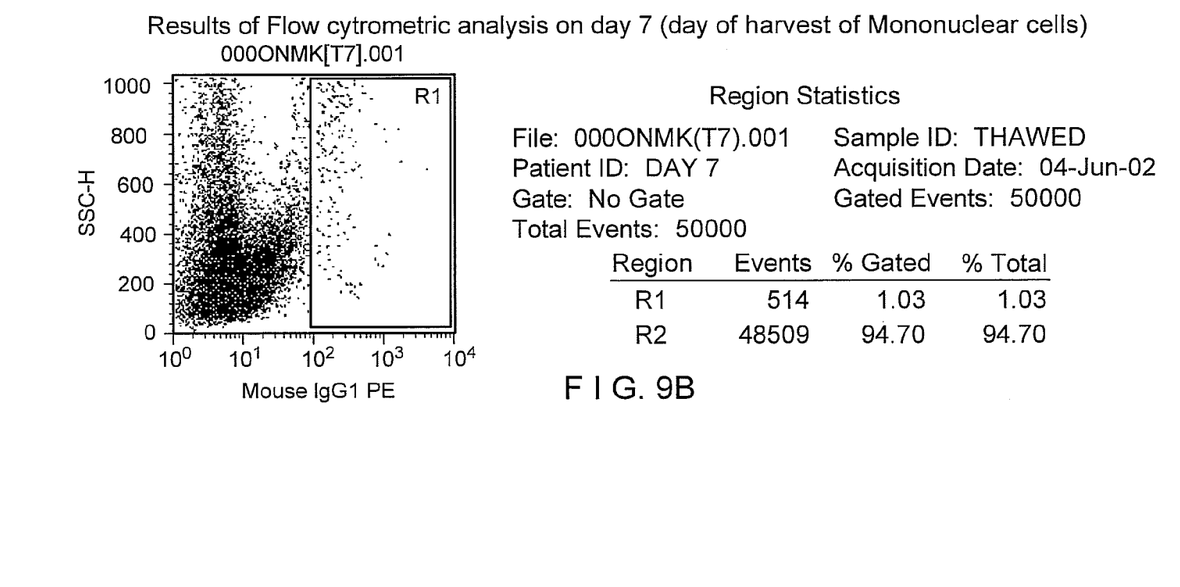
Figure 9C:
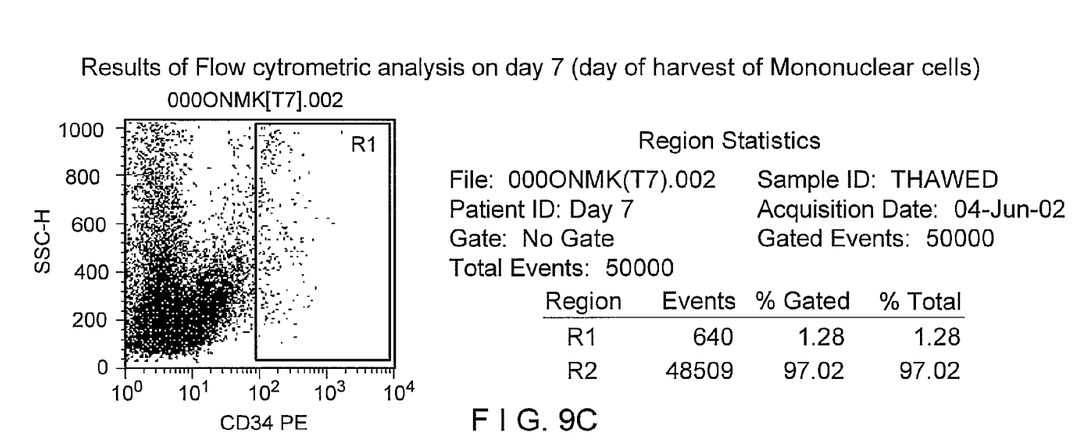
Figure 9D:
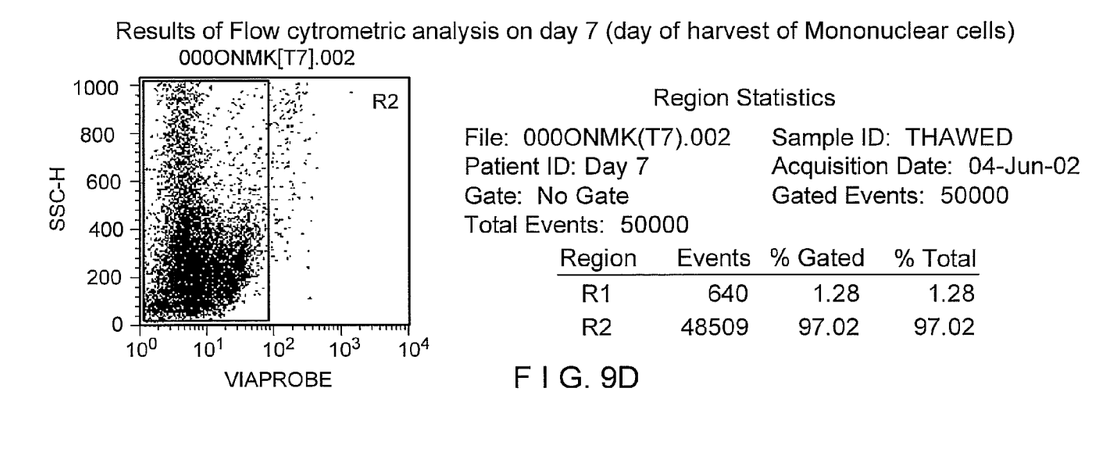

In the embodiments shown in FIGS. 1 and 3, a sterilized bioreactor system, is shown for ex vivo expansion of stem cells This is mainly useful for growing the cells in a three dimensional structure identical to that of the bone marrow microenvironment.

As shown in FIG. 1, the bio-reactor of the invention is a portable pilot plant which is easily sterilizable even in the assembled form. This assembly consists of a funnel shaped inlet (1) for media, connected to a reservoir (4) provided with two additive points (6). The reservoir (4) is provided with one inlet (4b) and two outlets (4a) and (4c) with a pinch cork (5) for the media to flow at a controlled level with a scaffolding material (17) placed 1 mm above the base.

The outlet (4a) for the media is held with clamps (19) so as to control the flow of the medium as required in the invention. The outlet (4a) is connected to the reactor vessels (9) with a T connector (7). (4c) is the outlet for sampling media from reservoir (4). (4b) is the inlet for additive into the reservoir.

The reactor vessel (9) basically consists of single or multiple circular vessels such as petriplates with diameter varying between 55 mm–100 mm mounted on support (18). These petriplates are made up of glass or polycarbonate with a funnel shaped reactor cover (8). A capillary (11) is fused to the reactor cover (8) which allows a slow inflow of the media. The length of the capillary (11) is such that, the drops of the media are prevented from falling directly on the scaffold (17), instead the media drops get absorbed by the scaffold (17). This process prevents the shear that may be caused to the cells due to the direct fall of the drops of media. Scaffold (17) is made up of biocompatible matrix like polymer such as Nitrocellulose or bio-ceramic. Scaffold (17) provides three dimensional space for the stem cells to grow and interact. It also provides easy penetration of gases and fluids needed for stem cell growth without undergoing differentiation and the consequent loss of "stemness".

The outlet tubing (12) of reactor vessel (9) is connected by Y connector (10) to an inlet of the waste media collector (13). The outflow of the media from the reactor vessel (9) is gravity dependent.

A sampling port (14) is provided at the bottom of the waste media collector (13) for collecting the aliquots of the used media for sampling. These samples are used for testing the amount of media components used in the growth of cells The entire assembly of the reactor is made up of glass. This assembly is enclosed in a Perspex cassette/cover (16). This makes sit an individual entity by itself.

A gas inlet (15a) is provided on the cassette/cover (16) for entry of gases as per the requirement. A gas outlet (15b) is provided for exchange of gases.

It is due to the unique design of the present device that it is easy to use, safe and economically viable.

EXAMPLE

The following example is represented to illustrate the invention but do not limit the scope thereof.

Analysis of the experiments conducted by the present inventors to validate the expansion of haemopoietic stem cells using the bio reactor of the present invention is given below in the tabular form.

TABULATION OF THE RESULTS WITH BIOREACTOR

| Experiment Number | Number of nucleated cells seeded on Day 0 | Number of nucleated cells harvested on Day 7 | Fold difference in nucleated counts | Absolute count of CD34+ cells on Day 0 | Absolute count of CD34+ cells on Day 7 | Fold difference in absolute counts of CD34+ cells |
|---|---|---|---|---|---|---|
| 1. | $1 \times 10^6$ cells | $0.2 \times 10^6$ cells | 0.2 fold decrease | Not done | Not done | — |
| 2. | $1 \times 10^6$ cells | $0.3 \times 10^6$ cells | 0.3 fold decrease | Not done | Not done | — |
| 3. | $1 \times 10^6$ cells | $2 \times 10^6$ cells | 2 fold increase | $2.9 \times 10^3$ CD34+ cells | $3.2 \times 10^3$ CD34+ cells | 1.1 fold increase |
| 4. | $2.5 \times 10^6$ cells | $7.2 \times 10^6$ cells | 2.9 fold increase | $2.5 \times 10^3$ CD34+ cells | $14.4 \times 10^3$ CD34+ cells | 5.7 fold increase |
| 5. | $2.5 \times 10^6$ cells | $8.5 \times 10^6$ cells | 3.4 fold increase | $2.5 \times 10^3$ CD34+ cells | $21.2 \times 10^3$ CD34+ cells | 8.5 fold increase |

It is observed that the number of nucleated cells is increased to the extent of 3 fold. Also the CD34+ cells have shown increase in the number as compared to 0 day. The increase was from 1.1 fold to 8.5 fold. This shows that by our invention CD34+ stem cells can be expanded to 8.5 folds.

Flow cytometry was performed on cord blood samples expanded in bioreactor of the present invention, using various growth factors.

FIG. 8, gives the Flow cytometric dot clot representation of the results of the expansion of stem cells in the bioreactor of the present invention. It is can be seen from the representation, that the viability of stem cells on 0 day was above 94.02% and that 0.14% of the nucleated cells were CD34+ cells.

The entire assembly of the reactor is made up of glass. This assembly is enclosed in a Perspex cassette/cover (16). "Perspex" defines material which is plastic available in thick sheets. This makes it an individual entity by itself.

We claim:

1. A sterilizable bio-reactor system for ex vivo expansion of haemopoietic stem cells derived from Umbilical Cord Blood to provide a portable pilot plant, comprising:
    at least one pair of reactor culture assemblies, each said reactor culture assembly including at least one vessel and a cover, and each said reactor assembly having a separate inlet port and a separate outlet port;
    a single case and a carbon dioxide incubator for each said at least one pair of reactor culture assemblies;
    each said reactor culture assembly being maintained in said single case and kept in said carbon dioxide incubator, thereby enabling other assemblies to be mounted in said carbon dioxide incubator without disturbing the assemblies already in said single case;
    a scaffolding material positioned on a base of each said reactor culture assembly to provide a micro environment either identical to or substantially identical to the micro environment in human bone marrow whereby self-renewal property of haemopoietic stem cells remain intact and do not lose their self-renewal property;
    a reservoir and two additive points to said reservoir and an outlet for each said reactor culture assembly; and,
    fitting the reactor culture assembly in said case, and said case being provided with a gas inlet and then keeping the reactor culture assembly in said carbon dioxide incubator configured to receive and condition the reactor culture assembly during different stages of the cell growth processes whereby different reactor culture assembly can be fitted within different cases so that more than one reactor culture assemblies can be mounted in a carbon dioxide incubator without disturbing the other reactor assemblies.

2. The system according to claim 1, wherein said reactor assembly is a three-dimensional structure and includes at least one of said vessels identical to or substantially equivalent to a bone marrow micro environment and provides for cultivating the stem cells in an inert bio-compatible scaffold and includes a capillary to prevent drops of media from falling directly onto said scaffolding material, thereby preventing shear to the cells due to a direct fall of the drops of the media onto said scaffolding material.

3. The system according to claim 1, wherein the reactor vessel comprises a least one circular vessel having a diameter varying between 55 mm to 100 mm and a cover, and said reactor vessel is a petri plate formed of glass or polycarbonate, and a capillary fused to said cover for allowing a slow inflow of the media, and the system enables the use of proteolytic enzymes which enable modification of stem call surface characteristics thereby enabling graft in narrow spaces.

4. The system according to claim 3, wherein the scaffolding material is bio-compatible and made up of bio-compatible matrix like polymer formed of nitrocellulose, and by being located on the base of the culture vessel provides for the micro environment substantially identical to that present in the human bone marrow.

5. The system according to claim 1, wherein the scaffolding material is bio-compatible and made up of bio-compatible matrix like polymer formed of nitrocellulose, and by being located on the base of the culture vessel provides for the micro environment substantially identical to that present in the human bone marrow.

6. The system according to claim 1, wherein the scaffolding material is porous and is provided with sufficient internal space for stem cells to grow and to interact and for easy penetration of gases and fluids needed for stem cell growth, and the scaffold has a property of complexing in a specific way with protein needed for stem cell renewal.

7. The system according to claim 1 wherein the system provides for expansion in vitro to effect long term repopulating haemopoietic stem cells and includes close cell to cell interaction.

8. The system according to claim 1, including providing for a supply of mobilizing oxygen and carbon dioxide for maintaining gas tension for optimal expansion of haemopoietic stem cells without comprising their self-renewability.

9. The system according to claim 1, including means for supplying mobilizing oxygen and carbon dioxide to said reactor assembly, and means for circulation of media containing micro and macro nutrients and growth factors such that gradients essential for haemotopoietic stem cells expansion are established within said reactor assembly without comprising their self-renewal properly.

10. The system according to claim 1, including fitting the reactor assembly in a thick sheet plastic case provided with a gas inlet and then keeping the reactor assembly in a carbon dioxide incubator configured to receive and condition the reactor assembly during different stages of the cell growth processes whereby different reactor assemblies can be fitted within different cases so that more than one can be mounted in a carbon dioxide incubator without disturbing the reactor assemblies already in said case, said case providing for an environment to permit expansion of the haemopoietic stem cells without losing their stemness.

11. The system according to claim 1, wherein said case is a thick sheet plastic case for said reactor assembly for fitting thereof within said case, a gas inlet to said reactor assembly for supplying mobilizing oxygen and said carbon dioxide to the haemopoietic stem cells for maintainlng gas tension for optimal expansion.

12. A sterilizable bio-reactor device, comprising
    a pair of reactor culture assemblies each including a reactor vessel and a cover having an individual inlet capillary fused thereto;
    each said reactor vessel being maintained in a case and kept in a carbon dioxide incubator, thereby enabling other reactor culture assemblies to be mounted in said carbon dioxide incubator without disturbing other assemblies;
    a scaffolding material positioned on a base of each said reactor vessel to provide a microenvironment either identical to or substantially identical to the micro environment in human bone marrow;

a single media feed to a reservoir having more than one outlet, one for each said reactor culture assembly;

two additive points to said reservoir; and, each said reactor vessel being provided with an outlet gravity dependent to a waste media collector.

13. The device according to claim 12, wherein the reactor assembly is a three-dimensional structure identical to or substantially equivalent to a bone marrow micro environment, and comprises at least one circular vessel having a diameter varying between 55 mm to 100 mm;

said reactor vessel being a petri plate formed of glass or polycarbonate;

each said individual inlet capillary fused to an individual one of said covers for permitting a slow inflow of media while preventing drops of the media from falling directly onto said scaffolding material thereby preventing shear caused to cells as a result of a direct fall of the drops onto the media;

the scaffold being bio-compatible and being made up of a bio-compatible matrix like polymer formed of nitrocellulose; and, said scaffolding material positioned on the base of the culture vessel provides for the micro environment being substantially identical to that present in the human bone marrow, and said scaffolding material being porous and provided with sufficient internal space for stem cells to grow.

14. The device according to claim 12, wherein the said reactor vessel is a petri plate formed of glass or polycarbonate and said inlet capillary fused to said cover permitting the slow inflow of media while preventing drops of the media from falling directly onto said scaffolding material thereby preventing shear caused to cells as a result of a direct fall of the drops onto the media, the same scaffold being bio-compatible and being made up of bio-compatible matrix like polymer formed of nitrocellulose or bioceramic, and said scaffolding material located on the base of the culture vessel provides for a micro environment substantially identical to that present in the human bone marrow, and said scaffolding material being porous and provided with sufficient internal space for stem cells to grow, the reactor chamber being enclosed such that cells do not get washed out.

15. The device according to claim 14, including a plurality of said reactor assemblies, and a thick sheet plastic case for each said plurality of reactor assemblies, a gas inlet to each said thick sheet plastic case for maintenance thereby in a carbon dioxide incubator configured to receive and condition each said reactor assembly during different stages of cell growth, whereby to avoid modification of surface characteristics of the stem cell, and to supply mobilizing oxygen and carbon dioxide to the haemopoietic stem cells for maintaining gas tension for optunal expansion for circulation media, and including providing for observation through said case timelines of direct transplantation of the stem cells together with the scaffolding material.

16. The device according to claim 12 including means for supplying mobilizing oxygen and carbon dioxide to said reactor assembly, and means for circulation of media containing micro and macro nutrients and growth factors such that gradients essential for haemotopoietic stem cells expansion are established within said reactor assembly, a thick sheet plastic case for said reactor assembly provided with a gas inlet and then keeping the reactor assembly in a carbon dioxide incubator configured to receive and condition the reactor assembly during different stages of the cell growth processes whereby different reactor assemblies can be fitted within different cases so that more than one can be mounted in a carbon dioxide incubator without disturbing other reactor assemblies and to assist by provision of an environment for said haemopoietic.

* * * * *